(12) United States Patent
Appel et al.

(10) Patent No.: US 6,537,959 B2
(45) Date of Patent: Mar. 25, 2003

(54) BLEACH CATALYST AND COMPOSITION AND METHOD FOR BLEACHING A SUBSTRATE

(75) Inventors: Adrianus Cornelis Appel, Vlaardingen (NL); Ronald Hage, Vlaardingen (NL); Stephen William Russell, Bedford (GB); David Tetard, Wirral (GB)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 130 days.

(21) Appl. No.: 09/851,276

(22) Filed: May 8, 2001

(65) Prior Publication Data

US 2002/0049148 A1 Apr. 25, 2002

(30) Foreign Application Priority Data

May 12, 2000 (GB) .............................. 0011527

(51) Int. Cl.[7] .............................. C11D 7/32; C11D 7/38; C11D 7/54
(52) U.S. Cl. ................... 510/311; 510/303; 510/372; 510/376; 510/500; 8/111; 502/200; 252/186.33; 252/186.39
(58) Field of Search ................. 510/303, 311, 510/372, 376, 500; 8/111; 502/200; 252/186.33, 186.39

(56) References Cited

U.S. PATENT DOCUMENTS

| 3,332,882 A | 7/1967 | Blumbergs et al. ......... 252/186 |
|---|---|---|
| 4,128,494 A | 12/1978 | Schirmann et al. ......... 252/186 |
| 4,144,226 A | 3/1979 | Crutchfield et al. ........ 528/231 |
| 4,146,495 A | 3/1979 | Crutchfield et al. ...... 528/89 R |
| 4,397,757 A | 8/1983 | Bright et al. ........... 252/186.41 |
| 4,412,934 A | 11/1983 | Chung et al. ........... 252/186.41 |
| 4,675,393 A | 6/1987 | Coxon ....................... 536/18.6 |
| 4,751,015 A | 6/1988 | Humphreys et al. .......... 252/99 |

FOREIGN PATENT DOCUMENTS

| DE | 3337921 | 10/1983 |
|---|---|---|
| EP | 0 120 591 | 2/1984 |
| EP | 0 174 132 | 8/1985 |
| EP | 0 185 522 | 12/1985 |
| EP | 0 284 292 | 3/1988 |
| EP | 0 303 520 | 8/1988 |
| GB | 836988 | 6/1960 |
| GB | 864798 | 4/1961 |
| GB | 907356 | 10/1962 |
| GB | 1003310 | 9/1965 |
| GB | 1 519 351 | 7/1978 |
| WO | 00/60044 | 10/2000 |

OTHER PUBLICATIONS

Chemical and Pharmaceutical Bulletin, Pharmaceutical Society of Japan, vol. 8, No. 43, 1995, pp. 1464–378, XP–002077996.

*Primary Examiner*—Gregory DelCotto
(74) *Attorney, Agent, or Firm*—Milton L. Honig

(57) ABSTRACT

Compounds are provided that may be used as ligands in transition metal complexes, in turn useful as bleach catalysts. Also provided are complexes, bleaching compositions and methods of using the compounds.

16 Claims, No Drawings

BLEACH CATALYST AND COMPOSITION AND METHOD FOR BLEACHING A SUBSTRATE

This invention relates to compositions and methods for catalytically bleaching substrates, more particularly using a defined class of ligand or complex as catalyst, and further relates to ligands and complexes useful in such compositions and methods.

Peroxygen bleaches are well known for their ability to remove stains from substrates. Traditionally, the substrate is subjected to hydrogen peroxide, or to substances which can generate hydroperoxyl radicals, such as inorganic or organic peroxides. Generally, these systems must be activated. One method of activation is to employ wash temperatures of 60° C. or higher. However, these high temperatures often lead to inefficient cleaning, and can also cause premature damage to the substrate.

A preferred approach to generating hydroperoxyl bleach radicals is the use of inorganic peroxides coupled with organic precursor compounds. These systems are employed for many commercial laundry powders. For example, various European systems are based on tetraacetyl ethylenediamine (TAED) as the organic precursor coupled with sodium perborate or sodium percarbonate, whereas in the United States laundry bleach products are typically based on sodium nonanoyloxybenzenesulfonate (SNOBS) as the organic precursor coupled with sodium perborate.

Precursor systems are generally effective but still exhibit several disadvantages. For example, organic precursors are moderately sophisticated molecules requiring multi-step manufacturing processes resulting in high capital costs. Also, precursor systems have large formulation space requirements so that a significant proportion of a laundry powder must be devoted to the bleach components, leaving less room for other active ingredients and complicating the development of concentrated powders. Moreover, precursor systems do not bleach very efficiently in countries where consumers have wash habits entailing low dosage, short wash times, cold temperatures and low wash liquor to substrate ratios.

Alternatively, or additionally, hydrogen peroxide and peroxy systems can be activated by bleach catalysts, such as by complexes of iron and the ligand N4Py (i.e. N,N-bis (pyridin-2-yl-methyl)-bis(pyridin-2-yl)methylamine) disclosed in WO95/34628, or the ligand Tpen (i.e. N,N,N',N'-tetra(pyridin-2-yl-methyl)ethylenediamine) disclosed in WO97/48787.

Although many types of bleach catalysts are known in the art, nevertheless there still remains a need for further classes of bleach catalysts.

According to WO95/34628 or WO97/48787, molecular oxygen may be used as the oxidant as an alternative to peroxide generating systems. However, no role in catalysing bleaching by atmospheric oxygen in an aqueous medium is reported. It has long been thought desirable to be able to use atmospheric oxygen (air) as the source for a bleaching species, as this would avoid the need for costly hydroperoxyl generating systems. Unfortunately, air as such is kinetically inert towards bleaching substrates and exhibits no bleaching ability. Recently some progress has been made in this area. For example, WO 97/38074 reports the use of air for oxidising stains on fabrics by bubbling air through an aqueous solution containing an aldehyde and a radical initiator. A broad range of aliphatic, aromatic and heterocyclic aldehydes is reported to be useful, particularly para-substituted aldehydes such as 4-methyl-, 4-ethyl- and 4-isopropyl benzaldehyde, whereas the range of initiators disclosed includes N-hydroxysuccinimide, various peroxides and transition metal coordination complexes.

However, although this system employs molecular oxygen from the air, the aldehyde component and radical initiators such as peroxides are consumed during the bleaching process. These components must therefore be included in the composition in relatively high amounts so as not to become depleted before completion of the bleaching process in the wash cycle. Moreover, the spent components represent a waste of resources as they can no longer participate in the bleaching process.

Accordingly, it would be desirable to be able to provide a bleaching system based on atmospheric oxygen or air that does not need to rely primarily on hydrogen peroxide or a hydroperoxyl generating system, and that does not require the presence of organic components such as aldehydes that are consumed in the process. Furthermore, it would be desirable to be able to provide a bleaching system that is capable of being based either on atmospheric oxygen/air or on hydrogen peroxide/hydroperoxyl-generating systems as a source of the primary bleaching species, or on both. Moreover, it would be desirable to provide such bleaching systems that are effective in aqueous medium.

It may also be noted that the known art teaches a bleaching effect only as long as the substrate is being subjected to the bleaching treatment. Thus, there is no expectation that hydrogen peroxide or peroxy bleach systems could continue to provide a bleaching effect on a treated substrate, such as a laundry fabric after washing and drying, since the bleaching species themselves or any activators necessary for the bleaching systems would be assumed to be removed from the substrate, or consumed or deactivated, on completing the wash cycle and drying.

It would be therefore also be desirable to be able to treat a textile such that, after the treatment is completed, a bleaching effect is observed on the textile. Furthermore, it would be desirable to be able to provide a bleach treatment for textiles such as laundry fabrics whereby residual bleaching occurs when the treated fabric has been treated and is dry.

We have found that a selected class of ligand or complex is surprisingly effective in catalysing the bleaching of substrates, either using atmospheric oxygen or air, or using hydrogen peroxide or a hydroperoxyl generating system, or using both. Furthermore, we have found certain novel ligands and complexes which are useful in the bleaching of substrates.

Accordingly, in a first aspect, the present invention provides a compound of the general formula (I):

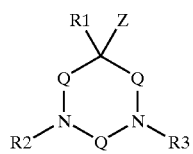

wherein

Z represents a group selected from —NH$_2$, —NHR$^4$, —N(R$^4$)$_2$, —N(R$^4$)$_3$$^+$, —NO$_2$, —NHC(O)R$^4$, —N(R$^4$)C(O)R$^4$ (wherein R$^4$ represents alkyl, cycloalkyl, aryl, arylalkyl or heteroarylalkyl, each optionally substituted by —F, —Cl, —Br, —I, —NH$_3$$^+$, —SO$_3$H, —SO$_3$$^-$ (Na$^+$, K$^+$), —COOH, —COO$^-$(Na$^+$, K$^+$), —P(O)(OH)$_2$, or —P(O)(O$^-$(Na$^+$, K$^+$))$_2$), an optionally substituted heterocyclic ring or an optionally substituted heteroaromatic ring selected from pyridine, pyrimidine, pyrazine, pyrazole, imidazole, benzimidazole, quinoline, quinoxaline, triazole, isoquinoline, carbazole, indole, isoindole, oxazole and thiazole;

each Q independently represent a group of the formula:

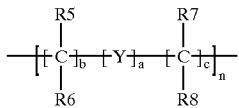

wherein $5 \geq a+b+c \geq 1$; $a=0-5$; $b=0-5$; $c=0-5$; $n=1$ or $2$;

Y independently represents a group selected from —O—, —S—, —SO—, —SO$_2$—, —C(O)—, arylene, alkylene, heteroarylene, heterocycloalkylene, —(G)P—, —P(O)— and —(G)N—, wherein G is selected from hydrogen, alkyl, aryl, arylalkyl, cycloalkyl, each except hydrogen being optionally substituted by one or more functional groups E;

R1, R2, R3, R5, R6, R7, R8 independently represent a group selected from hydrogen, hydroxyl, halogen, —R and —OR, wherein R represents alkyl, alkenyl, cycloalkyl, heterocycloalkyl, aryl, heteroaryl or a carbonyl derivative group, R being optionally substituted by one or more functional groups E, or R5 together with R6, or R7 together with R8, or both, represent oxygen, or R5 together with R7 and/or independently R6 together with R8, or R5 together with R8 and/or independently R6 together with R7, represent $C_{1-6}$-alkylene optionally substituted by $C_{1-4}$-alkyl, —F, —Cl, —Br or —I; and E independently represents a functional group selected from —F, —Cl, —Br, —I, —OH, —OR', —NH$_2$, —NHR', —N(R')$_2$, —N(R')$_3^+$, —C(O)R', —OC(O)R', —COOH, —COO$^-$(Na$^+$, K$^+$), —COOR', C(O)NH$_2$, —C(O)NHR', —C(O)N(R')$_2$, heteroaryl, —R', —SR', —SH, —P(R')$_2$, —P(O)(R')$_2$, —P(O)(OH)$_2$, —P(O)(OR')$_2$, —NO$_2$, —SO$_3$H, —SO$_3^-$(Na$^+$, K$^+$), —S(O)$_2$R', —NHC(O)R', and —N(R')C(O)R', wherein R' represents cycloalkyl, aryl, arylalkyl, or alkyl optionally substituted by —F, —Cl, —Br, —I, —NH$_3^+$, —SO$_3$H, —SO$_3^-$(Na$^+$, K$^+$), —COOH, —COO$^-$(Na$^+$, K$^+$), —P(O)(OH)$_2$, or —P(O)(O$^-$(Na$^+$, K$^+$))$_2$.

In a second aspect, the present invention provides a bleaching composition comprising, in an aqueous medium, atmospheric oxygen and a ligand which forms a complex with a transition metal, the complex catalysing bleaching of a substrate by the atmospheric oxygen, wherein the ligand is a compound as defined above and the aqueous medium is substantially devoid of peroxygen bleach or a peroxy-based or -generating system. The medium is therefore preferably insensitive or stable to catalase, which acts on peroxy species. Also provided in accordance with this second aspect is a method of bleaching a substrate comprising applying to the substrate, in an aqueous medium, a ligand which forms a complex with a transition metal, the complex catalysing bleaching of the substrate by atmospheric oxygen, wherein the ligand is a compound as defined above and the medium is substantially devoid of a peroxygen bleach or a peroxy-based or -generating system.

In a third aspect, the present invention provides a bleaching composition comprising, in an aqueous medium, a ligand which forms a complex with a transition metal, the complex catalysing bleaching of a substrate, and a peroxygen bleach or a peroxy-based or -generating system, wherein the ligand is a compound as defined above. Also provided in accordance with this third aspect is a method of bleaching a substrate comprising applying to the substrate, in an aqueous medium, a ligand which forms a complex with a transition metal, wherein the ligand is a compound as defined above and the medium comprises a peroxygen bleach or a peroxy-based or -generating system.

We have also found that certain ligands or complexes of this class are surprisingly effective in catalysing bleaching of the substrate by atmospheric oxygen after treatment of the substrate. Accordingly, in a fourth aspect, the present invention provides a method of treating a textile by contacting the textile with a ligand which forms a complex with a transition metal, whereby the complex catalyses bleaching of the textile by atmospheric oxygen after the treatment.

In a fifth aspect, the present invention provides a dry textile having a ligand as defined above applied or deposited thereon, whereby bleaching by atmospheric oxygen is catalysed on the textile.

Advantageously, the compounds of the present invention permit all or the majority of the bleaching species in the medium (on an equivalent weight basis) to be derived from atmospheric oxygen, if desired. By 'majority' is meant more than 50% so that if bleaching species derived from atmospheric oxygen are present in a concentration of for example 0.25 mM, other bleaching species may only be present at less than 0.25 mM. Thus, the medium can be made wholly or substantially devoid of peroxygen bleach or a peroxy-based or -generating bleach system. Furthermore, the complex is a catalyst for the bleaching process and, as such, is not consumed but can continue to participate in the bleaching process. The catalytically activated bleaching systems of the type in accordance with the present invention are therefore both cost-effective and environmentally friendly, particularly when based on atmospheric oxygen. Moreover, the bleaching system is operable under unfavourable wash conditions which include low temperatures, short contact times and low dosage requirements. Furthermore, the method is effective in an aqueous medium and is therefore particularly applicable to bleaching of laundry fabrics. Therefore, whilst the composition and method according to the present invention may be used for bleaching any suitable substrate, the preferred substrate is a laundry fabric. The bleaching method may be carried out by simply leaving the substrate in contact with the medium for a sufficient period of time. Preferably, however, the aqueous medium on or containing the substrate is agitated.

An advantage of the method according to the fourth aspect of the invention is that, by enabling a bleaching effect even after the textile has been treated, the benefits of bleaching can be prolonged on the textile. Furthermore, since a bleaching effect is conferred to the textile after the treatment, the treatment itself, such as a laundry wash cycle, may for example be shortened. Moreover, since a bleaching effect is achieved by atmospheric oxygen after treatment of the textile, hydrogen peroxide or peroxy-based bleach systems can be omitted from the treatment substance. In the general formula (I) above, preferably Z represents a group selected from —NH$_2$, —NHR$^4$, —N(R$^4$)$_2$, —N(R$^4$)$_3^+$, —NO$_2$, —NHC(O)R$^4$ and —N(R$^4$)C(O)R$^4$, preferably selected from —NH$_2$, —NHR$^4$, —N(R$^4$)$_2$, —N(R$^4$)$_3^+$ and —NO$_2$, wherein R$^4$ represents an optionally substituted group selected from alkyl, cycloalkyl, aryl, arylalkyl or heteroarylalkyl (wherein heteroaryl is selected from pyridine, pyrimidine, pyrazine, pyrazole, imidazole, benzimidazole, quinoline, quinoxaline, triazole, isoquinoline, carbazole, indole, isoindole, oxazole and thiazole), preferably an optioanlly substituted group selected from $C_{1-4}$-alkyl and heteroaryl-$C_{1-4}$-alkyl. Preferred optional substituents for $R^4$ are selected from —F, —Cl, —Br, —I, —$NH_3^+$, —$SO_3H$, —$SO_3^-(Na^+, K^+)$, —COOH, —$COO^-(Na^+, K^+)$, —$P(O)(OH)_2$, and —$P(O)(O^-(Na^+, K^+))_2$.

The groups R1, R2, R3, R5, R6, R7, R8 are preferably independently selected from —H, hydroxy-$C_0$–$C_{20}$-alkyl, halo-$C_0$–$C_{20}$-alkyl, nitroso, formyl-$C_0$–$C_{20}$-alkyl, carboxyl-$C_0$–$C_{20}$-alkyl and esters and salts thereof, carbamoyl-$C_0$–$C_{20}$-alkyl, sulfo-$C_0$–$C_{20}$-alkyl and esters and salts thereof, sulfamoyl-$C_0$–$C_{20}$-alkyl, amino-$C_0$–$C_{20}$-alkyl, aryl-$C_0$–$C_{20}$-alkyl, $C_0$–$C_{20}$-alkyl, alkoxy-$C_0$–$C_8$-alkyl, carbonyl-$C_0$–$C_6$-alkoxy, and $C_0$–$C_{20}$-alkylamide.

Each Q preferably is independently defined such that a=b=0, c=1 and n=1–4. More preferably, each Q independently represents $C_{1-4}$-alkylene, especially $C_{1-3}$-alkylene.

In preferred embodiments, in general formula (I) each Q independently represents $C_{1-4}$-alkylene, the group R1 represents methyl, groups R2 and R3 each independently represent hydrogen, methyl or optionally substituted pyridin-2-ylmethyl, and group $R^4$ represents methyl or optionally substituted pyridin-2-ylmethyl.

In a preferred embodiment, the compound has the general formula (II):

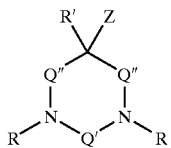

II wherein

Z represents —$NO_2$, —$NH_2$, or —NR"R"';

R' and R" independently represent —H or —$CH_3$;

each R and R"' independently represent —$CH_3$ or pyridin-2-ylmethyl;

Q' represents ethylene or n-propylene;

Q" represents methylene or ethylene.

More preferably, the compound is of the general formula (III):

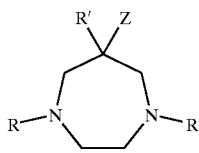

III wherein

Z represents —$NO_2$, —$NH_2$, or —NR"R"';

R' and R" independently represent —H or —$CH_3$;

each R and R"' independently represent —$CH_3$ or pyridin-2-ylmethyl.

If one or both of the R groups in formula (III) represent pyridin-2-ylmethyl and Z represents —NR"R"', then preferably R"' represents —$CH_3$.

Accordingly, in a first preferred embodiment of general formula (III):

Z represents —$NO_2$, —$NH_2$, or —NR"R"';

R' and each R represent —$CH_3$;

R" represents —H or —$CH_3$;

R"' represents —$CH_3$ or pyridin-2-ylmethyl.

In a preferred second embodiment of general formula (III):

Z represents —$NO_2$, —$NH_2$, or —NR"R"';

R' represents —$CH_3$;

each R represents pyridin-2-ylmethyl;

R" and R"' represent —$CH_3$.

Particularly preferred compounds include:

6-dimethylamino-1,4-bis(pyridin-2-ylmethyl)-6-methyl-1,4-diazacycloheptane;

6-amino-1,4-bis(pyridin-2-ylmethyl)-6-methyl-1,4-diazacycloheptane;

6-{N-(pyridin-2-ylmethyl)-N-methylamino}-1,4,6-trimethyl-1,4-diazacycloheptane;

6-amino-1,4,6-trimethyl-1,4-diazacycloheptane; and 6-dimethylamino-1,4,6-trimethyl-1,4-diazacycloheptane.

In a particularly preferred embodiment, the compound is 6-{N-(pyridin-2-ylmethyl)-N-methylamino}-1,4,6-trimethyl-1,4-diazacycloheptane:

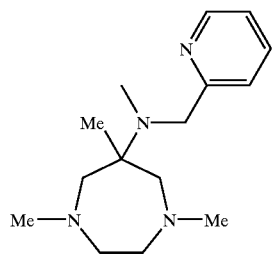

The compounds according to the present invention form complexes with transition metals, and thus may be used as ligands to form complexes that act as catalysts in bleaching compositions.

In the bleaching compositions, the ligand may be present as a preformed complex of a ligand and a transition metal. Alternatively, the composition may comprise a free ligand that complexes with a transition metal already present in the water or that complexes with a transition metal present in the substrate. The composition may also be formulated as a composition of a free ligand or a transition metal-substitutable metal-ligand complex, and a source of transition metal, whereby the complex is formed in situ in the medium.

The ligand forms a complex with one or more transition metals, in the latter case for example as a dinuclear complex. Suitable transition metals include for example: manganese in oxidation states II–V, iron II–V, copper I–III, cobalt I–III, titanium II–IV, tungsten IV–VI, vanadium II–V and molybdenum II–VI.

More particularly, the ligand forms a complex of the general formula (IV):

$$[M_aL_kX_n]Y_m \quad \text{(IV)}$$

in which:

M represents a metal selected from Mn(II)–(III)–(IV)–(V), Cu(I)–(II)–(III), Fe(II)–(III)–(IV)–(V), Co(I)–(II)–(III), Ti (II)–(III)–(IV), V(II)–(III)–(IV)–(V), Mo (II)–(III)–(IV)–(V)–(VI) and W(IV)–(V)–(VI), preferably selected from Fe(II)–(III)–(IV)–(V);

L represents a ligand as herein defined, or its protonated or deprotonated analogue;

X represents a coordinating species selected from any mono, bi or tri charged anions and any neutral molecules able to coordinate the metal in a mono, bi or tridentate manner, preferably selected from $O^{2-}$, $RBO_2^{2-}$, $RCOO^-$, $RCONR^-$, $OH^-$, $NO_3^-$, $NO$, $S^{2-}$, $RS^-$, $PO_4^{3-}$, $PO_3OR^{3-}$, $H_2O$, $CO_3^{2-}$, $HCO_3^-$, $ROH$, $N(R)_3$, $ROO^-$, $O_2^{2-}$, $O_2^-$, $RCN$, $Cl^-$, $Br^-$, $OCN^-$, $SCN^-$, $CN^-$, $N_3^-$, $F^-$, $I^-$, $RO^-$, $ClO_4^-$, and $CF_3SO_3^-$, and more preferably selected from $O^{2-}$, $RBO_2^{2-}$, $RCOO^-$, $OH^-$, $NO_3^-$, $S^{2-}$, $RS^-$, $PO_3^{4-}$, $H_2O$, $CO_3^{2-}$, $HCO_3^-$, $ROH$, $N(R)_3$, $Cl^-$, $Br^-$, $OCN^-$, $SCN^-$, $RCN$, $N_3^-$, $F^-$, $I^-$, $RO^-$, $ClO_4^-$, and $CF_3SO_3^-$;

Y represents any non-coordinated counter ion, preferably selected from $ClO_4^-$, $BR_4^-$, $[MX_4]^-$, $[MX_4]^{2-}$, $PF_6^-$, $RCOO^-$, $NO_3^-$, $RO^-$, $N^+(R)_4$, $ROO^-$, $O_2^{2-}$, $O_2^-$, $Cl^-$, $Br^-$, $F^-$, $I^-$, $CF_3SO_3^-$, $S_2O_6^{2-}$, $OCN^-$, $SCN^-$, $H_2O$, $RBO_2^{2-}$, $BF_4^-$ and $BPh_4^-$, and more preferably selected from $ClO_4^-$, $BR_4^-$, $[FeCl_4]^-$, $PF_6^-$, $RCOO^-$, $NO_3^-$, $RO^-$, $N^+(R)_4$, $Cl^-$, $Br^-$, $F^-$, $I^-$, $CF_3SO_3^-$, $S_2O_{62-}$, $OCN^-$, $SCN^-$, $H_2O$ and $BF_4^-$;

a represents an integer from 1 to 10, preferably from 1 to 4;

k represents an integer from 1 to 10;

n represents an integer from 1 to 10, preferably from 1 to 4;

m represents zero or an integer from 1 to 20, preferably from 1 to 8; and each R independently represents a group selected from hydrogen, hydroxyl, —R' and —OR', wherein R'=alkyl, alkenyl, cycloalkyl, heterocycloalkyl, aryl, heteroaryl or a carbonyl derivative group, R' being optionally substituted by one or more functional groups E, and preferably each R independently represents hydrogen, optionally substituted alkyl or optionally substituted aryl, more preferably hydrogen or optionally substituted phenyl, naphthyl or $C_{1-4}$-alkyl.

The counter ions Y in formula (IV) balance the charge z on the complex formed by the ligand L, metal M and coordinating species X. Thus, if the charge z is positive, Y may be an anion such as $RCOO^-$ $BPh_4^-$, $ClO_4^-$, $BF_4^-$, $PF_6^-$, $RSO_3^-$, $RSO_4^-$, $SO_4^{2-}$, $NO_3^-$, $F^-$, $Cl^-$, $Br^-$, or $I^-$, with R being hydrogen, optionally substituted alkyl or optionally substituted aryl. If z is negative, Y may be a common cation such as an alkali metal, alkaline earth metal or (alkyl) ammonium cation.

Suitable counter ions Y include those which give rise to the formation of storage-stable solids. Preferred counter ions for the preferred metal complexes are selected from $R^7COO^-$, $ClO_4^-$, $BF_4^-$, $PF_6^-$, $RSO_3^-$ (in particular $CF_3SO_3^-$), $RSO_4^-$, $SO_4^{2-}$, $NO_3^-$, $F^-$, $Cl^-$, $Br^-$, and $I^-$, wherein R represents hydrogen or optionally substituted phenyl, naphthyl or $C_1$–$C_4$ alkyl.

It will be appreciated that the complex (IV) can be formed by any appropriate means, including in situ formation whereby precursors of the complex are transformed into the active complex of general formula (IV) under conditions of storage or use. Preferably, the complex is formed as a well-defined complex or in a solvent mixture comprising a salt of the metal M and the ligand L or ligand L-generating species. Alternatively, the catalyst may be formed in situ from suitable precursors for the complex, for example in a solution or dispersion containing the precursor materials. In one such example, the active catalyst may be formed in situ in a mixture comprising a salt of the metal M and the ligand L, or a ligand L-generating species, in a suitable solvent. Thus, for example, if M is iron, an iron salt such as $FeSO_4$ can be mixed in solution with the ligand L, or a ligand L-generating species, to form the active complex. Thus, for example, the composition may formed from a mixture of the ligand L and a metal salt $MX_m$, in which preferably n=1–5, more preferably 1–3. In another such example, the ligand L, or a ligand L-generating species, can be mixed with metal M ions present in the substrate or wash liquor to form the active catalyst in situ. Suitable ligand L-generating species include metal-free compounds or metal coordination complexes that comprise the ligand L and can be substituted by metal M ions to form the active complex according the formula (IV).

The bleaching compositions according to the second and third aspects of the present invention may be used for laundry cleaning, hard surface cleaning (including cleaning of lavatories, kitchen work surfaces, floors, mechanical ware washing etc.). As is generally known in the art, bleaching compositions are also employed in waste-water treatment, pulp bleaching during the manufacture of paper, leather manufacture, dye transfer inhibition, food processing, starch bleaching, sterilisation, whitening in oral hygiene preparations and/or contact lens disinfection.

In the context of the present invention bleaching should be understood as relating generally to the decolourisation of stains or of other materials attached to or associated with a substrate. However, it is envisaged that the present invention can be applied where a requirement is the removal and/or neutralisation by an oxidative bleaching reaction of malodours or other undesirable components attached to or otherwise associated with a substrate. Furthermore, in the context of the present invention bleaching is to be understood as being restricted to any bleaching mechanism or process that does not require the presence of light or activation by light. Thus, photobleaching compositions and processes relying on the use of photobleach catalysts or photobleach activators and the presence of light are excluded from the present invention.

In typical washing compositions the level of the catalyst is such that the in-use level is from 0.05 $\mu$M to 50 mM, with preferred in-use levels for domestic laundry operations falling in the range 0.5 $\mu$M to 100 $\mu$M, more preferably from 1 $\mu$M to 10 $\mu$M. Higher levels may be desired and applied in industrial bleaching processes, such as textile and paper pulp bleaching.

Preferably, the aqueous medium has a pH in the range from pH 6 to 13, more preferably from pH 6 to 11, still more preferably from pH 8 to 11, and most preferably from pH 8 to 10, in particular from pH 9 to 10.

According to the bleaching compositions and methods according to the second aspect of the present invention, on the one hand, the composition or the medium in which the bleaching is conducted will be substantially devoid of a peroxygen bleach or a peroxy-based or -generating system.

Whilst this second aspect of the present invention is based on the catalytic bleaching of a substrate by atmospheric oxygen or air, it will be appreciated that small amounts of hydrogen peroxide or peroxy-based or -generating systems may be included in the composition, if desired. Therefore, by "substantially devoid of peroxygen bleach or peroxy-based or -generating bleach systems" is meant that the composition contains from 0 to 50%, preferably from 0 to 10%, more preferably from 0 to 5%, and optimally from 0 to 2% by molar weight on an oxygen basis, of peroxygen bleach or peroxy-based or -generating bleach systems. Preferably, however, the composition will be wholly devoid of peroxygen bleach or peroxy-based or -generating bleach systems. Thus, at least 10%, preferably a majority i.e. greater than 50%, and optimally at least 90% of any bleaching of the substrate is effected by oxygen sourced from the air.

According to the bleaching compositions and methods according to the third aspect of the present invention, on the other hand, the composition or the medium in which the bleaching is conducted will contain a peroxygen bleach or a peroxy-based or -generating system. The peroxy bleach may be a compound which is capable of yielding hydrogen peroxide in aqueous solution. Hydrogen peroxide sources are well known in the art. They include the alkali metal peroxides, organic peroxides such as urea peroxide, and inorganic persalts, such as the alkali metal perborates, percarbonates, perphosphates persilicates and persulphates. Mixtures of two or more such compounds may also be suitable.

Particularly preferred are sodium perborate tetrahydrate and, especially, sodium perborate monohydrate. Sodium perborate monohydrate is preferred because of its high active oxygen content. Sodium percarbonate may also be preferred for environmental reasons.

Another suitable hydrogen peroxide.generating system is a combination of a $C_1$–$C_4$ alkanol oxidase and a $C_1$–$C_4$ alkanol, especially a combination of methanol oxidase (MOX) and ethanol. Such combinations are disclosed in WO-A-9507972, which is incorporated herein by reference.

Alkylhydroxy peroxides are another class of peroxy bleaching compounds. Examples of these materials include cumene hydroperoxide and t-butyl hydroperoxide.

Organic peroxyacids may also be suitable as the peroxy bleaching compound. Such materials normally have the general formula:

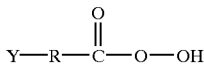

wherein R is an alkyl- or alkylidene- or substituted alkylene group containing from 1 to about 20 carbon atoms, optionally having an internal amide linkage; or a phenylene or substituted phenylene group; and Y is hydrogen, halogen, alkyl, aryl, an imido-aromatic or non-aromatic group, a —COOH or —COOOH group or a quaternary ammonium group.

Typical monoperoxy acids useful herein include, for example:

(i) peroxybenzoic acid and ring-substituted peroxybenzoic acids, e.g. peroxy-a-naphthoic acid;
(ii) aliphatic, substituted aliphatic and arylalkyl monoperoxyacids, e.g. peroxylauric acid, peroxystearic acid and N,N-phthaloylaminoperoxy caproic acid (PAP); and
(iii) 6-octylamino-6-oxo-peroxyhexanoic acid.

Typical diperoxyacids useful herein include, for example:

(iv) 1,12-diperoxydodecanedioic acid (DPDA);
(v) 1,9-diperoxyazelaic acid;
(vi) diperoxybrassylic acid; diperoxysebacic acid and diperoxyisophthalic acid;
(vii) 2-decyldiperoxybutane-1,4-dioic acid; and
(viii) 4,4'-sulphonylbisperoxybenzoic acid.

Also inorganic peroxyacid compounds are suitable, such as for example potassium monopersulphate (MPS). If organic or inorganic peroxyacids are used as the peroxygen compound, the amount thereof will normally be within the range of about 2–10% by weight, preferably from 4–8% by weight.

Generally, the composition can be suitably formulated to contain from 1 to 40%, preferably from 1 to 20%, more preferably from 1 to 15%, and most preferably from 1 to 10% by weight of the composition, of the peroxy bleaching agent.

Peroxyacid bleach precursors are known and amply described in literature, such as in GB-A-836988; GB-A-864, 798; GB-A-907,356; GB-A-1,003,310 and GB-A-1,519, 351; DE-A-3,337,921; EP-A-0,185,522; EP-A-0,174,132; EP-A-0,120,591; and U.S. Pat. No. 1,246,339; U.S. Pat. No. 3,332,882; U.S. Pat. No. 4,128,494; U.S. Pat. No. 4,412,934 and U.S. Pat. No. 4,675,393.

Another useful class of peroxyacid bleach precursors is that of the cationic i.e. quaternary ammonium substituted peroxyacid precursors as disclosed in U.S. Pat. No. 4,751, 015 and U.S. Pat. No. 4,397,757, in EP-A-0,284,292 and EP-A-331,229. Examples of peroxyacid bleach precursors of this class are:

2-(N,N,N-trimethyl ammonium) ethyl sodium-4-sulphophenyl carbonate chloride—(SPCC);
N-octyl,N,N-dimethyl-$N_{10}$-carbophenoxy decyl ammonium chloride—(ODC);
3-(N,N,N-trimethyl ammonium)propyl sodium-4-sulphophenyl carboxylate; and
N,N,N-trimethyl ammonium toluyloxy benzene sulphonate.

A further special class of bleach precursors is formed by the cationic nitriles as disclosed in EP-A-303,520; EP-A-458,396 and EP-A-464,880.

Of the above classes of bleach precursors, the preferred classes are the esters, including acyl phenol sulphonates and acyl alkyl phenol sulphonates; the acyl-amides; and the quaternary ammonium substituted peroxyacid precursors including the cationic nitriles.

Examples of said preferred peroxyacid bleach precursors or activators are sodium-4-benzoyloxy benzene sulphonate (SBOBS); N,N,N'N'-tetraacetyl ethylene diamine (TAED); sodium-1-methyl-2-benzoyloxy benzene-4-sulphonate; sodium-4-methyl-3-benzoloxy benzoate; 2-(N,N,N-trimethyl ammonium)ethyl sodium-4-sulphophenyl carbonate chloride (SPCC); trimethyl ammonium toluyloxybenzene sulphonate; sodium nonanoyloxybenzene sulphonate (SNOBS); sodium 3,5,5-trimethyl hexanoyloxybenzene sulphonate (STHOBS); and the substituted cationic nitriles. The peracid precursor TAED is particularly preferred.

The precursors may be used in an amount of up to 12%, preferably from 2–10%, by weight of the composition according to the third aspect.

The bleaching compositions according to the second and third aspects of the present invention have particular application in detergent formulations, especially for laundry cleaning. Accordingly, the present invention also provides detergent bleach compositions comprising bleaching compositions as defined above and additionally a surface-active material, optionally together with detergency builder.

The bleach compositions may for example contain a surface-active material in an amount of from 10 to 50% by weight. The surface-active material may be naturally derived, such as soap, or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch.

Typical synthetic anionic surface-actives are usually water-soluble alkali metal salts of organic sulfates and sulfonates having alkyl groups containing from about 8 to about 22 carbon atoms, the term "alkyl" being used to include the alkyl portion of higher aryl groups. Examples of suitable synthetic anionic detergent compounds are sodium and ammonium alkyl sulfates, especially those obtained by sulfating higher ($C_8$–$C_{18}$) alcohols produced, for example, from tallow or coconut oil; sodium and ammonium alkyl ($C_9$–$C_{20}$) benzene sulfonates, particularly sodium linear secondary alkyl ($C_{10}$–$C_{15}$) benzene sulfonates; sodium alkyl glyceryl ether sulfates, especially those ethers of the higher alcohols derived from tallow or coconut oil fatty acid monoglyceride sulfates and sulfonates; sodium and ammonium salts of sulfuric acid esters of higher ($C_9$–$C_{18}$) fatty alcohol alkylene oxide, particularly ethylene oxide, reaction products; the reaction products of fatty acids such as coconut fatty acids esterified with isethionic acid and neutralised with sodium hydroxide; sodium and ammonium salts of fatty acid amides of methyl taurine; alkane monosulfonates such as those derived by reacting alphaolefins ($C_8$–$C_{20}$) with sodium bisulfite and those derived by reacting paraffins with $SO_2$ and $Cl_2$ and then hydrolysing with a base to produce a random sulfonate; sodium and ammonium ($C_7$–$C_{12}$) dialkyl sulfosuccinates; and olefin sulfonates, which term is used to describe material made by reacting olefins, particularly ($C_{10}$–$C_{20}$) alpha-olefins, with $SO_3$ and then neutralising and hydrolysing the reaction product. The preferred anionic detergent compounds are sodium ($C_{10}$–$C_{15}$) alkylbenzene sulfonates, and sodium ($C_{16}$–$C_{18}$) alkyl ether sulfates.

Examples of suitable nonionic surface-active compounds which may be used, preferably together with the anionic surface-active compounds, include, in particular, the reaction products of alkylene oxides, usually ethylene oxide, with alkyl ($C_6$–$C_{22}$) phenols, generally 5–25 EO, i.e. 5–25 units of ethylene oxides per molecule; and the condensation products of aliphatic ($C_8$–$C_{18}$) primary or secondary linear or branched alcohols with ethylene oxide, generally 2–30 EO. Other so-called nonionic surface-actives include alkyl polyglycosides, sugar esters, long-chain tertiary amine oxides, long-chain tertiary phosphine oxides and dialkyl sulfoxides.

Amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

The detergent bleach compositions of the invention will preferably comprise from 1 to 15% wt of anionic surfactant and from 10 to 40% by weight of nonionic surfactant. In a further preferred embodiment, the detergent active system is free from $C_{16}$–$C_{12}$ fatty acid soaps.

The bleach compositions of the present invention may also contains a detergency builder, for example in an amount of from about 5 to 80% by weight, preferably from about 10 to 60% by weight.

Builder materials may be selected from 1) calcium sequestrant materials, 2) precipitating materials, 3) calcium ion-exchange materials and 4) mixtures thereof.

Examples of calcium sequestrant builder materials include alkali metal polyphosphates, such as sodium tripolyphosphate; nitrilotriacetic acid and its water-soluble salts; the alkali metal salts of carboxymethyloxy succinic acid, ethylene diamine tetraacetic acid, oxydisuccinic acid, mellitic acid, benzene polycarboxylic acids, citric acid; and polyacetal carboxylates as disclosed in U.S. Pat. No. 4,144,226 and U.S. Pat. No. 4,146,495.

Examples of precipitating builder materials include sodium orthophosphate and sodium carbonate.

Examples of calcium ion-exchange builder materials include the various types of water-insoluble crystalline or amorphous aluminosilicates, of which zeolites are the best known representatives, e.g. zeolite A, zeolite B (also known as zeolite P), zeolite C, zeolite X, zeolite Y and also the zeolite P-type as described in EP-A-0,384,070.

In particular, the compositions of the invention may contain any one of the organic and inorganic builder materials, though, for environmental reasons, phosphate builders are preferably omitted or only used in very small amounts. Typical builders usable in the present invention are, for example, sodium carbonate, calcite/carbonate, the sodium salt of nitrilotriacetic acid, sodium citrate, carboxymethyloxy malonate, carboxymethyloxy succinate and water-insoluble crystalline or amorphous aluminosilicate builder materials, each of which can be used as the main builder, either alone or in admixture with minor amounts of other builders or polymers as co-builder.

In the compositions and methods according to the third aspect of the present invention, when using a hydrogen peroxide source, such as sodium perborate or sodium percarbonate, as the bleaching compound, it is preferred that the composition contains not more than 5% by weight of a carbonate buffer, expressed as sodium carbonate, more preferable not more than 2.5% by weight to substantially nil, if the composition pH lies in the lower alkaline region of up to 10.

Apart from the components already mentioned, the bleach compositions of the present invention can contain any of the conventional additives in amounts of which such materials are normally employed in fabric washing detergent compositions. Examples of these additives include buffers such as carbonates, lather boosters, such as alkanolamides, particularly the monoethanol amides derived from palmkernel fatty acids and coconut fatty acids; lather depressants, such as alkyl phosphates and silicones; anti-redeposition agents, such as sodium carboxymethyl cellulose and alkyl or substituted alkyl cellulose ethers; stabilisers, such as phosphonic acid derivatives (i.e. Dequest® types); fabric softening agents; inorganic salts and alkaline buffering agents, such as sodium sulfate and sodium silicate; and, usually in very small amounts, fluorescent agents; perfumes; enzymes, such as proteases, cellulases, lipases, amylases and oxidases; germicides and colourants.

In the compositions and methods according to the second aspect of the present invention, transition metal sequestrants such as EDTA, and phosphonic acid derivatives such as EDTMP (ethylene diamine tetra(methylene phosphonate)) may also be included, in addition to the ligand specified, for example to improve the stability sensitive ingredients such as enzymes, fluorescent agents and perfumes, but provided the composition remains bleaching effective. However, the compositions according to the second aspect of the present invention, containing the ligand, preferably are substantially, and more preferably completely, devoid of transition metal sequestrants (other than the ligand). On the other hand, transition metal sequestrants such as EDTA and the phosphonic acid derivatives such as EDTMP are of special importance to the compositions and methods according to the third aspect of the present invention, as not only do they improve the stability of the catalyst/$H_2O_2$ system and sensitive ingredients, such as enzymes, fluorescent agents, perfumes and the like, but also improve the bleach performance, especially at the higher pH region of above 10, particularly at pH 10.5 and above. Other suitable transition metal sequestrants are known and can be chosen by those skilled in the art, for example aminocarboxylates, aminophosphonates, and polyfunctionally substituted aromatic chelating agents, as disclosed further in WO-A-98/39406. If present, the sequestrants are generally present in amounts of 0.001 to 15%, more preferably 0.01 to 3.0%, by weight of the composition.

According to the fourth aspect, the catalyst may be contacted to the textile fabric in any suitable manner. For example, it may be applied in dry form, such as in powder form, or in a liquor that is then dried, for example as an aqueous spray-on fabric treatment fluid or a wash liquor for laundry cleaning, or a non-aqueous dry cleaning fluid or spray-on aerosol fluid. Other suitable means of contacting the catalyst to the textile may be used, as further explained below.

Any suitable textile that is susceptible to bleaching or one that one might wish to subject to bleaching may be used. Preferably the textile is a laundry fabric or garment.

The bleaching method of the fourth aspect may be carried out by simply leaving the substrate in contact with the catalyst for a sufficient period of time. Preferably, however, the catalyst is in an aqueous medium, and the aqueous medium on or containing the substrate is agitated.

In a preferred embodiment, the treated textile is dried, by allowing it to dry under ambient temperature or at elevated temperatures.

In a particularly preferred embodiment the method according to the fourth aspect is carried out on a laundry fabric using aqueous treatment liquor. In particular the treatment may be effected in, or as an adjunct to, an essentially conventional wash cycle for cleaning laundry. More preferably, the treatment is carried out in an aqueous detergent wash liquor. The catalyst can be delivered into the wash liquor from a powder, granule, pellet, tablet, block, bar or other such solid form. The solid form can comprise a carrier, which can be particulate, sheet-like or comprise a three-dimensional object. The carrier can be dispersible or soluble in the wash liquor or may remain substantially intact. In other embodiments, the catalyst can be delivered into the wash liquor from a paste, gel or liquid concentrate.

It is particularly advantageous that the catalyst used in the method of the fourth aspect makes use of atmospheric oxygen in its bleaching activity. This avoids the requirement that peroxygen bleaches and/or other relatively large quantities of reactive substances need be used in the treatment process. Consequently, only a relatively small quantity of bleach active substance need be employed and this allows dosage routes to be exploited which could previously not be used. Thus, while it is preferable to include the catalyst in a composition that is normally used in a washing process, such as a pre-treatment, main-wash, conditioning composition or ironing aid, other means for ensuring that the catalyst is present in the wash liquor may be envisaged.

For example, it is envisaged that the catalyst can be presented in the form of a body from which it is slowly released during the whole or part of the laundry process. Such release can occur over the course of a single wash or over the course of a plurality of washes. In the latter case it is envisaged that the catalyst can be released from a carrier substrate used in association with the wash process, e.g. from a body placed in the dispenser drawer of a washing machine, elsewhere in the delivery system or in the drum of the washing machine. When used in the drum of the washing machine the carrier can be freely moving or fixed relative to the drum. Such fixing can be achieved by mechanical means, for example by barbs that interact with the drum wall, or employ other forces, for example a magnetic force. The modification of a washing machine to provide for means to hold and retain such a carrier is envisaged similar means being known from the analogous art of toilet block manufacture. Freely moving carriers such as shuttles for dosage of surfactant materials and/or other detergent ingredients into the wash can comprise means for the release of the catalyst into the wash.

In the alternative, the catalyst can be presented in the form of a wash additive that preferably is soluble. The additive can take any of the physical forms used for wash additives, including powder, granule, pellet, sheet, tablet, block, bar or other such solid form or take the form of a paste, gel or liquid. Dosage of the additive can be unitary or in a quantity determined by the user. While it is envisaged that such additives can be used in the main washing cycle, the use of them in the conditioning or drying cycle is not hereby excluded.

The present invention is not limited to those circumstances in which a washing machine is employed, but can be applied where washing is performed in some alternative vessel. In these circumstances it is envisaged that the catalyst can be delivered by means of slow release from the bowl, bucket or other vessel which is being employed, or from any implement which is being employed, such as a brush, bat or dolly, or from any suitable applicator.

Suitable pre-treatment means for application of the catalyst to the textile material prior to the main wash include sprays, pens, roller-ball devices, bars, soft solid applicator sticks and impregnated cloths or cloths containing microcapsules. Such means are well known in the analogous art of deodorant application and/or in spot treatment of textiles. Similar means for application are employed in those embodiments where the catalyst is applied after the main washing and/or conditioning steps have been performed, e.g. prior to or after ironing or drying of the cloth. For example, the catalyst may be applied using tapes, sheets or sticking plasters coated or impregnated with the substance, or containing microcapsules of the substance. The catalyst may for example be incorporated into a drier sheet so as to be activated or released during a tumble-drier cycle, or the substance can be provided in an impregnated or microcapsule-containing sheet so as to be delivered to the textile when ironed.

Throughout the description and claims generic groups have been used, for example alkyl, alkoxy, aryl. Unless otherwise specified the following are preferred group restrictions that may be applied to generic groups found within compounds disclosed herein:

alkyl: linear and branched C1–C8-alkyl, alkenyl: C2–C6-alkenyl, cycloalkyl: C3–C8-cycloalkyl, alkoxy: C1–C6-alkoxy, alkylene: selected from the group consisting of: methylene; 1,1-ethylene; 1,2-ethylene; 1,1-propylidene; 1,2-propylene; 1,3-propylene; 2,2-propylidene; butan-2-ol-1,4-diyl; propan-2-ol-1,3-diyl; 1,4-butylene; cyclohexane-1,1-diyl; cyclohexan-1,2-diyl; cyclohexan-1,3-diyl; cyclohexan-1,4-diyl; cyclopentane-1,1-diyl; cyclopentan-1,2-diyl; and cyclopentan-1,3-diyl, aryl: selected from homoaromatic compounds having a molecular weight under 300, arylene: selected from the group consisting of: 1,2-phenylene; 1,3-phenylene; 1,4-phenylene; 1,2-naphtalenylene; 1,3-naphtalenylene; 1,4- naphtalenylene; 2,3-naphtalenylene; 1-hydroxy-2,3-phenylene; 1-hydroxy-2,4-phenylene; 1-hydroxy-2,5-phenylene; and 1-hydroxy-2,6-phenylene, heteroaryl: selected from the group consisting of: pyridinyl; pyrimidinyl; pyrazinyl; triazolyl; pyridazinyl; 1,3,5-triazinyl; quinolinyl; isoquinolinyl; quinoxalinyl; imidazolyl; pyrazolyl; benzimidazolyl; thiazolyl; oxazolidinyl; pyrrolyl; carbazolyl; indolyl; and isoindolyl, wherein the heteroaryl may be connected to the compound via any atom in the ring of the selected heteroaryl, heteroarylene: selected from the group consisting of: pyridindiyl; quinolindiyl; pyrazodiyl; pyrazoldiyl; triazolediyl; pyrazindiyl; and imidazolediyl, wherein the heteroarylene acts as a bridge in the compound via any atom in the ring of the selected heteroarylene, more specifically preferred are: pyridin-2,3-diyl; pyridin-2,4-diyl; pyridin-2,5-diyl; pyridin-2,6-diyl; pyridin-3,4-diyl; pyridin-3,5-diyl; quinolin-2,3-diyl; quinolin-2,4-diyl; quinolin-2,8-diyl; isoquinolin-1,3-diyl; isoquinolin-1,4-diyl; pyrazol-1,3-diyl; pyrazol-3,5-diyl; triazole-3,5-diyl; triazole-1,3-diyl; pyrazin-2,5-diyl; and imidazole-2,4-diyl, heterocycloalkyl: selected from the group consisting of: pyrrolinyl; pyrrolidinyl; morpholinyl; piperidinyl; piperazinyl; hexamethylene imine; 1,4-piperazinyl; tetrahydrothiophenyl; tetrahydrofuranyl; 1,4,7-triazacyclononanyl; 1,4,8,11-tetraazacyclotetradecanyl; 1,4,7,10,13-pentaazacyclopentadecanyl; 1,4-diaza-7-thiacyclononanyl; 1,4-diaza-7-oxa-cyclononanyl; 1,4,7,10-tetraazacyclododecanyl; 1,4-dioxanyl; 1,4,7-trithiacyclononanyl; tetrahydropyranyl; and oxazolidinyl, wherein the heterocycloalkyl may be connected to the compound via any atom in the ring of the selected heterocycloalkyl, heterocycloalkylene: selected from the group consisting of: piperidin-1,2-ylene; piperidin-2,6-ylene; piperidin-4,4-ylidene; 1,4-piperazin-1,4-ylene; 1,4-piperazin-2,3-ylene; 1,4-piperazin-2,5-ylene; 1,4-piperazin-2,6-ylene; 1,4-piperazin-1,2-ylene; 1,4-piperazin-1,3-ylene; 1,4-piperazin-1,4-ylene; tetrahydrothiophen-2,5-ylene; tetrahydrothiophen-3,4-ylene; tetrahydrothiophen-2,3-ylene; tetrahydrofuran-2,5-ylene; tetrahydrofuran-3,4-ylene; tetrahydrofuran-2,3-ylene; pyrrolidin-2,5-ylene; pyrrolidin-3,4-ylene; pyrrolidin-2,3-ylene; pyrrolidin-1,2-ylene; pyrrolidin-1,3-ylene; pyrrolidin-2,2-ylidene; 1,4,7-triazacyclonon-1,4-ylene; 1,4,7-triazacyclonon-2,3-ylene; 1,4,7-triazacyclonon-2,9-ylene; 1,4,7-triazacyclonon-3,8-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,5-ylene; 1,4,8,11-tetraazacyclotetradec-1,2-ylene; 1,4,8,11-tetraazacyclotetradec-2,2-ylidene; 1,4,7,10-tetraazacyclododec-1,4-ylene; 1,4,7,10-tetraazacyclododec-1,7-ylene; 1,4,7,10-tetraazacyclododec-1,2-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4,7,10,13-pentaazacyclopentadec-2,3-ylene; 1,4,7,10,13-pentaazacyclopentadec-1,2-ylene; 1,4,7,10,13-pentaazacyclopentadec-2,2-ylidene; 1,4-diaza-7-thia-cyclonon-1,4-ylene; 1,4-diaza-7-thia-cyclonon-1,2-ylene; 1,4-diaza-7-thia-cyclonon-2,3-ylene; 1,4-diaza-7-thia-cyclonon-6,8-ylene; 1,4-diaza-7-thia-cyclonon-2,2-ylidene; 1,4-diaza-7-oxa-cyclonon-1,4-ylene; 1,4-diaza-7-oxa-cyclonon-1,2-ylene; 1,4-diaza-7-oxa-cyclonon-2,3-ylene; 1,4-diaza-7-oxa-cyclonon-6,8-ylene; 1,4-diaza-7-oxa-cyclonon-2,2-ylidene; 1,4-dioxan-2,3-ylene; 1,4-dioxan-2,6-ylene; 1,4-dioxan-2,2-ylidene; tetrahydropyran-2,3-ylene; tetrahydropyran-2,6-ylene; tetrahydropyran-2,5-ylene; tetrahydropyran-2,2-ylidene; 1,4,7-trithia-cyclonon-2,3-ylene; 1,4,7-trithia-cyclonon-2,9-ylene; and 1,4,7-trithiacyclonon-2,2-ylidene, amine: the group —N(R)$_2$ wherein each R is independently selected from: hydrogen; C1–C6-alkyl; C1–C6-alkyl-C6H5; and phenyl, wherein when both R are C1–C6-alkyl both R together may form an —NC3 to an —NC5 heterocyclic ring with any remaining alkyl chain forming an alkyl substituent to the heterocyclic ring, halogen: selected from the group consisting of: F; Cl; Br and I, sulfonate: the group —S(O)$_2$OR, wherein R is selected from: hydrogen; C1–C6-alkyl; phenyl; C1–C6-alkyl-C6H5; Li; Na; K; Cs; Mg; and Ca, sulfate: the group —OS(O)$_2$OR, wherein R is selected from: hydrogen; C1–C6-alkyl; phenyl; C1–C6-alkyl-C6H5; Li; Na; K; Cs; Mg; and Ca, sulfone: the group —S(O)$_2$R, wherein R is selected from: hydrogen; C1–C6-alkyl; phenyl; C1–C6-alkyl-C6H5 and amine (to give sulfonamide) selected from the group: —NR'2, wherein each R' is independently selected from: hydrogen; C1–C6-alkyl; C1–C6-alkyl-C6H5; and phenyl, wherein when both R' are C1–C6-alkyl both R' together may form an —NC3 to an —NC5 heterocyclic ring with any remaining alkyl chain forming an alkyl substituent to the heterocyclic ring, carboxylate derivative: the group —C(O)OR, wherein R is selected from: hydrogen; C1–C6-alkyl; phenyl; C1–C6-alkyl-C6H5; Li; Na; K; Cs; Mg; and Ca, carbonyl derivative: the group —C(O)R, wherein R is selected from: hydrogen; C1–C6-alkyl; phenyl; C1–C6-alkyl-C6H5 and amine (to give amide) selected from the group: —NR'2, wherein each R' is independently selected from:

hydrogen; C1–C6-alkyl; C1–C6-alkyl-C6H5; and phenyl, wherein when both R' are C1–C6-alkyl both R' together may form an —NC3 to an —NC5 heterocyclic ring with any remaining alkyl chain forming an alkyl substituent to the heterocyclic ring, phosphonate: the group —P(O)(OR)$_2$, wherein each R is independently selected from: hydrogen; C1–C6-alkyl; phenyl; C1–C6-alkyl-C6H5; Li; Na; K; Cs; Mg; and Ca, phosphate: the group —OP(O)(OR)$_2$, wherein each R is independently selected from: hydrogen; C1–C6-alkyl; phenyl; C1–C6-alkyl-C6H5; Li; Na; K; Cs; Mg; and Ca, phosphine: the group —P(R)$_2$, wherein each R is independently selected from: hydrogen; C1–C6-alkyl; phenyl; and C1–C6-alkyl-C6H5, phosphine oxide: the group —P(O)R$_2$, wherein R is independently selected from: hydrogen; C1–C6-alkyl; phenyl; and C1–C6-alkyl-C6H5; and amine (to give phosphonamidate) selected from the group: —NR'2, wherein each R' is independently selected from: hydrogen; C1–C6-alkyl; C1–C6-alkyl-C6H5; and phenyl, wherein when both R' are C1–C6-alkyl both R' together may form an —NC3 to an —NC5 heterocyclic ring with any remaining alkyl chain forming an alkyl substituent to the heterocyclic ring.

Unless otherwise specified the following are more preferred group restrictions that may be applied to groups found within compounds disclosed herein:

alkyl: linear and branched C1–C6-alkyl, alkenyl: C3–C6-alkenyl, cycloalkyl: C6–C8-cycloalkyl, alkoxy: C1–C4-alkoxy, alkylene: selected from the group consisting of: methylene; 1,2-ethylene; 1,3-propylene; butan-2-ol-1,4-diyl; 1,4-butylene; cyclohexane-1,1-diyl; cyclohexan-1,2-diyl; cyclohexan-1,4-diyl; cyclopentane-1,1-diyl; and cyclopentan-1,2-diyl, aryl: selected from group consisting of: phenyl; biphenyl; naphthalenyl; anthracenyl; and phenanthrenyl, arylene: selected from the group consisting of: 1,2-phenylene; 1,3-phenylene; 1,4-phenylene; 1,2-naphtalenylene; 1,4-naphtalenylene; 2,3-naphtalenylene and 1-hydroxy-2,6-phenylene, heteroaryl: selected from the group consisting of: pyridinyl; pyrimidinyl; quinolinyl; pyrazolyl; triazolyl; isoquinolinyl; imidazolyl; and oxazolidinyl, wherein the heteroaryl may be connected to the compound via any atom in the ring of the selected heteroaryl, heteroarylene: selected from the group consisting of: pyridin-2,3-diyl; pyridin-2,4-diyl; pyridin-2,6-diyl; pyridin-3,5-diyl; quinolin-2,3-diyl; quinolin-2,4-diyl; isoquinolin-1,3-diyl; isoquinolin-1,4-diyl; pyrazol-3,5-diyl; and imidazole-2,4-diyl, heterocycloalkyl: selected from the group consisting of: pyrrolidinyl; morpholinyl; piperidinyl; piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and piperazinyl, wherein the heterocycloalkyl may be connected to the compound via any atom in the ring of the selected heterocycloalkyl, heterocycloalkylene: selected from the group consisting of: piperidin-2,6-ylene; piperidin-4,4-ylidene; 1,4-piperazin-1,4-ylene; 1,4-piperazin-2,3-ylene; 1,4-piperazin-2,6-ylene; tetrahydrothiophen-2,5-ylene; tetrahydrothiophen-3,4-ylene; tetrahydrofuran-2,5-ylene; tetrahydrofuran-3,4-ylene; pyrrolidin-2,5-ylene; pyrrolidin-2,2-ylidene; 1,4,7-triazacyclonon-1,4-ylene; 1,4,7-triazacyclonon-2,3-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,2-ylidene; 1,4,7,10-tetraazacyclododec-1,4-ylene; 1,4,7,10-tetraazacyclododec-1,7-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4-diaza-7-thia-cyclonon-1,4-ylene; 1,4-diaza-7-thia-cyclonon-2,3-ylene; 1,4-diaza-7-thia-cyclonon-2,2-ylidene; 1,4-diaza-7-oxa-cyclonon-1,4-ylene; 1,4-diaza-7-oxa-cyclonon-2,3-ylene; 1,4-diaza-7-oxa-cyclonon-2,2-ylidene; 1,4-dioxan-2,6-ylene; 1,4-dioxan-2,2-ylidene; tetrahydropyran-2,6-ylene; tetrahydropyran-2,5-ylene; and tetrahydropyran-2,2-ylidene, amine: the group —N(R)$_2$, wherein each R is independently selected from: hydrogen; C1–C6-alkyl; and benzyl, halogen: selected from the group consisting of: F and Cl, sulfonate: the group —S(O)$_2$OR, wherein R is selected from: hydrogen; C1–C6-alkyl; Na; K; Mg; and Ca, sulfate: the group —OS(O)$_2$OR, wherein R is selected from: hydrogen; C1–C6-alkyl; Na; K; Mg; and Ca, sulfone: the group —S(O)$_2$R, wherein R is selected from: hydrogen; C1–C6-alkyl; benzyl and amine selected from the group: —NR'2, wherein each R' is independently selected from: hydrogen; C1–C6-alkyl; and benzyl, carboxylate derivative: the group —C(O)OR, wherein R is selected from hydrogen; Na; K; Mg; Ca; C1–C6-alkyl; and benzyl, carbonyl derivative: the group: —C(O)R, wherein R is selected from: hydrogen; C1–C6-alkyl; benzyl and amine selected from the group: —NR'2, wherein each R' is independently selected from: hydrogen; C1–C6-alkyl; and benzyl, phosphonate: the group —P(O)(OR)$_2$, wherein each R is independently selected from: hydrogen; C1–C6-alkyl; benzyl; Na; K; Mg; and Ca, phosphate: the group —OP(O)(OR)$_2$, wherein each R is independently selected from: hydrogen; C1–C6-alkyl; benzyl; Na; K; Mg; and Ca, phosphine: the group —P(R)$_2$, wherein each R is independently selected from: hydrogen; C1–C6-alkyl; and benzyl, phosphine oxide: the group —P(O)R$_2$, wherein R is independently selected from: hydrogen; C1–C6-alkyl; benzyl and amine selected from the group: —NR'2, wherein each R' is independently selected from: hydrogen; C1–C6-alkyl; and benzyl.

The invention will now be further illustrated by way of the following non-limiting examples:

EXAMPLES

Syntheses of the Compounds

6-Nitro-1,4,6-trimethyl-1,4-diazacycloheptane

N,N'-dimethyl-ethylenediamine (6.98 g, 81 mmol) and nitroethane (6.08 g, 82 mmol) were mixed and cooled in an ice-bath. Formaldehyde (aqueous 37%, 13.37 g, 165 mmol) was added dropwise at a temperature of 20–30° C. At this point the reaction mixture was pale yellow. It was heated in an oil bath at 95° C. for 10 min whereupon it became red-brown. It was cooled, water (approx. 10 ml) added and the organic phase extracted twice with ether. The bright yellow water layer was discarded and the combined ether layers dried (Na$_2$SO$_4$), filtered and evaporated to leave a red oil (14.5 g). This was short-path distilled to give the nitro-diazacycloheptane as a slightly yellow oil (12.8 g, 84%) b.p. 110° C./0.1 mm. IR (film) 1538 (s), 1457 (m), 1087 (m) cm$^{-1}$. $^1$H NMR (CDCl$_3$) δ 1.47 s(3H), 2.40 s(6H), 2.58 m(4H), 2.75 and 3.38 (AB system). $^{13}$C NMR (CDCl$_3$) δ 25.18, 48.77, 61.23, 65.71, 91.43. MS (ESP+) 188.1 [M+H]$^+$.

6-Amino-1,4,6-trimethyl-1,4-diazacycloheptane

6-Nitro-1,4,6-trimethyldiazacycloheptane (13.1 g, 70 mmol) was was dissolved in absolute ethanol (20 ml) and 2 spatulas of Raney nickel added. The mixture was hydrogenated at approx. 1.1 atmospheres hydrogen pressure until no more hydrogen was taken up. It was filtered over a small pad of Celite and the filtrate evaporated and distilled to give the free amine as a colourless oil (7.95 g, 72%) b.p.>70° C./0.1 mm. IR (film) 3348 (s), 2945 (s), 2813 (s), 1670 (m), 1538 (m), 1462 (s), 1376 (m), 1284 (m), 1093 (s) cm$^{-1}$. $^1$H NMR (CDCl$_3$) δ 1.00 s(3H), 2.32 s(6H), 2.28 and 2.44 and 2.63, 3 m (10H including N—H). $^{13}$C NMR (CDCl$_3$) δ 26.37, 48.91, 52.54, 60.35, 71.17. MS (FAB+) 158.1 [M+H]$^+$.

1,4,6-Trimethyl-6-(pyridin-2-ylmethylamino)-1,4-diazacycloheptane 6-Amino-1,4,6-trimethyl-1,4-diazacycloheptane (1.57 g, 10 mmol) was dissolved in methanol (30 ml) and pyridine-2-aldehyde (0.95 g, 10 mmol) was added. It became pale yellow. After stirring for 30 min it was cooled in water and sodium tetraborate 10 aq (2.0 g) was added followed by sodium borohydride (1.0 g) with cooling in a water bath. The mixture was acidified with 6N HCl then extracted with CH$_2$Cl$_2$ (discarded).). The aqueous phase was made basic with NH$_4$OH and extracted with CH$_2$Cl$_2$. The CH$_2$Cl$_2$ was dried and evaporated to leave a pale yellow oil (1.5 g).

$^1$H NMR (CDCl$_3$) δ (ppm) 0.95 s(3H), 2.26 s(6H), 2.35 (3 multiplets, 4H), 2.53 (2 multiplets, 4H), 3.80 (s, 2H), 7.03 m(1H), 7.30 m(1H), 7.52 m(1H), 8.43 m(1H). $^{13}$C NMR (CDCl$_3$) δ 23.53, 47.87, 48.96, 55.96, 60.80, 68.23, 121.59, 122.20, 136.29, 148.98, 160.72. MS (APCI$^+$) 249.3 [M+H]$^+$.

1,4,6-Trimethyl-6-{N-(pyridin-2-ylmethyl)-N-methylamino}-1,4-diazacycloheptane

6-Amino-1,4,6-trimethyl-diazacycloheptane (540 mg, 2.29 mmol) was dissolved in acetonitrile (3 ml) and 37% formaldehyde (1.11 g, 14 mmol) added. Acetic acid was added to give a pH of approx. 5 then sodium cyanoborohydride (1.03 g, 16.3 mmol) was added in portions. The temperature rose to 30–40° C. and more acetic acid was added to keep the pH at approx. 5. When the addition was complete it was stirred then acetic acid was added until the mixture was homogeneous then it was left overnight. 6N HCl was added and the mixture evaporated almost to dryness. Water was added and it was reevaporated. Water was added and was made basic with NH$_4$OH and extracted twice with toluene. The toluene was dried and evaporated to leave a pale yellow oil (640 mg). This was columned on silica gel with a gradient of 0–20% methanol in CH$_2$Cl$_2$. This gave the title product (300 mg) as a pale yellow oil. $^1$H NMR (CDCl$_3$) δ (ppm) 1.09 s(3H), 2.17 s(3H), 2.30 s(6H), 2.52 (2 br doublets, 6H), and 2.52 (2s, 2H), 3.93 (s, 2H), 7.08 m(1H), 7.39 m(1H), 7.60 m(1H), 8.46 m(1H). $^{13}$C NMR (CDCl$_3$) δ 36.03, 48.94, 57.44, 60.01, 61.83, 66.24, 121.48, 122.31, 136.44, 148.75.

6-Dimethylamino-1,4,6-trimethyl-1,4-diazacycloheptane (MEDACH)

6-Amino-1,4,6-trimethyl-1,4-diazacycloheptane (1.0 g, 6.4 mmol) was dissolved in acetonitrile (20 ml) and formaldehyde (aqueous 37%, 2.5 ml, 31 mmol) added. Sodium cyanoborohydride (630 mg, 10 mmol) was then added. The temperature rose to approx. 55° C. then dropped back and a "toffee" separated. After stirring for a total of 15 min, glacial acetic acid (approx. 1.0 ml) was added dropwise until wet pH paper showed a pH of approx. 6.5. This gave a pale brown mixture which was stirred for a further 30 min then left overnight at room temperature. A few more drops of acetic acid were added then it was evaporated to dryness, reevaporated with water and the residue taken up in water and made basic (pH>12) with 40% NaOH and extracted thrice with ether. The combined ether layers were washed with NaOH then extracted with approx. 1N HCl. The water layer was brought to pH>12 with 40% NaOH and extracted with ether. The combined ether extracts were dried and evaporated to leave the permethylated amine as a colourless oil (950 mg, 80%). IR (film) 2939 (s), 2800 (s), 1461 (s), 1375 (m), 1287 (m), 1149 (m), 1093 (s), 970 (m) cm$^{-1}$., $^1$H NMR (CDCl$_3$) δ 0.94 (s, 3H), 2.25 (s, 6H), 2.29 (s, 6H), 2.42–2.56 (m, 4H), 2.22, 2.68 (AB, J=15 Hz, 4H). $^{13}$C NMR (CDCl$_3$) δ 20.80, 39.53, 49.52, 59.94, 62.49, 66.54. MS (FAB+) 186.1 [M+H]$^+$.

6-Nitro-1,4-bis(pyridin-2-ylmethyl)-6-methyl-1,4-diazacycloheptane

N,N'-bis-(2-pyridylmethyl)-1,2-diaminoethane (5.61 g, 23.2 mmol) and nitroethane (1.74 g, 23.2 mmol) were mixed and cooled in an ice-bath. It became a stirrable paste and formaldehyde (aqueous 37%, 3.80 g, 46.9 mmol) was added dropwise at a temperature of 12–33° C. After only a small amount had been added it became homogeneous and remained so throughout the rest of the addition. At this point the reaction mixture was pale yellow. It was heated in an oil bath at 95° C. for 20 min whereupon it became light orange. It was cooled, water (approx. 25 ml) added and the organic phase extracted twice with ether and because tlc showed there was still unextracted material twice with toluene. The brown water layer was discarded and the combined ether and toluene extracts dried (Na$_2$SO$_4$), filtered and evaporated to leave a yellow oil (6.9 g). This was columned on silica with 0–5% methanol in CH$_2$Cl$_2$ as eluent. This gave a first group of fractions which were almost pure (1.53 g), a group of pure fractions (2.66 g) and a group containing the desired ligand together with a more polar compound (1.35 g). Analysis of the 2.66 g fraction gave:

$^1$H NMR (CDCl$_3$) δ 1.27 s(3H), 2.62 m(4H), 2.98 and 3.58 (AB system) (4H), 3.81 q(4H), 7.10 m(2H), 7.36 m(2H), 7.59 m(2H), 8.46 m(2H). $^{13}$C NMR (CDCl$_3$) δ 24.22, 58.51, 63.53, 65.36, 91.54, 122.22, 123.21, 136.53, 148.87, 159.14. MS (ESP+) 342.2 [M+H]$^+$, 364.2 [M+Na]$^+$.

6-Amino-1,4-bis-(pyridin-2-ylmethyl)-6-methyl-1,4-diazacycloheptane

6-Nitro-diazacycloheptane (2.71 g, 7.9 mmol) was dissolved in absolute ethanol (15 ml) and 2 spatulas of Raney nickel added. The mixture was hydrogenated at approx. 4 atmospheres hydrogen pressure until no more hydrogen was taken up. It was filtered over a small pad of Celite and the filtrate evaporated to give the free amine as a brown oil (3.0 g, >100%) $^1$H NMR (CDCl$_3$) δ (ppm) 1.39 s(3H), 2.51 and 2.78 (AB system, 4H), 2.68 and 3.12 (AB system, 4H), 3.81 and 3.99 (AB system, 4H), 7.10 m(2H), 7.26 m(2H), 7.54 m(2H), 8.55 m(2H). $^{13}$C NMR (CDCl$_3$) δ 21.16, 54.96, 56.37, 63.41, 63.51, 122.27, 123.10, 136.74, 149.07, 158.68.

6-Dimethylamino-1,4-bis(pyridin-2-ylmethyl)-6-methyl-1,4-diazacycloheptane

6-Amino-diazacycloheptane (640 mg, 2.05 mmol) was dissolved in formic acid (3 ml) and 37% formaldehyde (2 ml) added. The mixture was heated in an oil bath at 100° C. overnight then 6N HCl was added and the mixture evaporated almost to dryness. Water was added and it was reevaporated. Water was added and it was extracted with CH$_2$Cl$_2$ (discarded). The aqueous phase was made basic with NH$_4$OH and extracted with toluene. The toluene was dried and evaporated to leave a pale yellow oil (500 mg).

$^1$H NMR (CDCl$_3$) δ (ppm) 0.91 s(3H), 2.23 s(6H), 2.42 and 2.99 (AB system, 4H), 2.48 and 2.53 (AB system, 4H), 3.68 and 3.80 (AB system, 4H), 7.08 m(2H), 7.46 m(2H), 7.59 m(2H), 8.48 m(2H). $^{13}$C NMR (CDCl$_3$) δ 23.06, 39.39, 59.51, 60.52, 63.54, 66.25, 121.88, 123.00, 136.30, 148.88, 160.01.

The following mixtures were prepared and tested for catalytic bleaching activity using air or H$_2$O$_2$:

Compound 1: 1,4,6-trimethyl-6-{N-(pyridin-2-ylmethyl)-N-methylamino}-1,4-diazacycloheptane +Mn(ClO$_4$)$_2$.6H$_2$O Compound 2: 1,4,6-trimethyl-6-{N-(pyridin-2-ylmethyl)-N-methylamino}-1,4-diazacycloheptane +Fe(ClO$_4$)$_2$.6H$_2$O Compound 3: 1,4,6-trimethyl-6-{N-(pyridin-2-ylmethyl)-N-methylamino}-1,4-diazacycloheptane +Co(ClO$_4$)$_2$.6H$_2$O

Example 1

As blanks, tomato-soya oil stained cloths were added to an aqueous solution containing 10 mM carbonate buffer (pH 10) with 0.6 g/l NaLAS (linear alkylbenzene sulphonate) or containing 10 mM borate buffer (pH 8) with 0.6 g/l NaLAS, and kept in contact with the solution under agitation for 30 minutes at 30° C. As examples of the invention, the same experiments were carried out but with the addition of a mixture of 10 μM of manganese (II) perchlorate and 20 μM of ligand, referred to in the table below.

After the wash, the cloths were rinsed with water and subsequently dried at 30° C. and the change in colour was measured immediately after drying with a Linotype-Hell scanner (ex Linotype). The change in colour (including bleaching) is expressed as the ΔE value. The measured colour difference (ΔE) between the washed cloth and the unwashed cloth is defined as follows:

$$\Delta E = [(\Delta L)^2 + (\Delta a)^2 + (\Delta b)^2]^{1/2}$$

wherein ΔL is a measure for the difference in darkness between the washed and unwashed test cloth; Δa and Δb are measures for the difference in redness and yellowness respectively between both cloths. With regard to this colour measurement technique, reference is made to Commission International de l'Eclairage (CIE); Recommendation on Uniform Colour Spaces, colour difference equations, psychometric colour terms, supplement no 2 to CIE Publication, no 15, Colormetry, Bureau Central de la CIE, Paris 1978. A higher ΔE value means a whiter cloth.

TABLE 1

|  | pH 8 + LAS | pH 10 + LAS |
|---|---|---|
| Blank | 4 | 5 |
| Compound 1 | 8 | 8 |

Example 2

Bleach values expressed in ΔE, as defined above. Stain: curry extract. Washed for 30 min at 30° C., rinsed, dried, stored for 24 h in the dark and measured. In all cases a mixture of 10 μM of metal (II) perchlorate salt and 20 μM of ligand complex was used in the wash liquor (except for blank).

The results are shown below in Table 2:

TABLE 2

|  | pH 8 − LAS | pH 8 + LAS | pH 10 − LAS | pH 10 + LAS |
|---|---|---|---|---|
| Blank | 7 | 9 | 19 | 19 |
| Compound 1 | 14 | 16 | 23 | 24 |

TABLE 2-continued

|  | pH 8 − LAS | pH 8 + LAS | pH 10 − LAS | pH 10 + LAS |
|---|---|---|---|---|
| Compound 2 | 18 | 19 | 28 | 28 |
| Compound 3 | 15 | 20 | 21 | 21 |

Example 3

Stain: BC-1 (tea stain). Washed for 30 min at 40° C. (no buffer), rinsed, dried in a tumble drier and measured. A mixture of 10 μM of manganese(II) perchlorate salt and 50 μM of the ligand complex (except for blank) was used in the wash liquor containing 10 mmol H$_2$O$_2$. After the wash, the cloths were dried in a tumble drier and the reflectance was measured with a Minolta 3700d spectrophotometer at 460 nm. The difference in reflectance before and after the wash is defined as ΔR460 value.

The results are shown below in Table 3:

TABLE 3

|  | ΔR460 |
|---|---|
| Blank | 7 |
| Compound 1 | 15 |

Example 4

Bleach values expressed in ΔE, as defined above. Stains: BC-1 (tea), curry-oil stain and tomato-oil stain. Compound 1 with 10 mM H$_2$O$_2$ at pH 10 with 0.6 g/l NaLAS was used for this series of experiments (with blank (only 10 mM H$_2$O$_2$) as reference) washed for 30 min at 30° C., rinsed, dried, and measured as discussed above.

The results are shown below in Table 4:

TABLE 4

| Stain | Blank = 10 mM H$_2$O$_2$ | Compound 1 + 10 mM H$_2$O$_2$ (*) |   |
|---|---|---|---|
| BC-1 | 2 | 4 | (4) |
| Curry | 13 | 28 | (28) |
| Tomato oil | 6 | 12 | (15) |

(*) Shows ΔE value after 24 h storage

The results presented in Tables 1–4 show that: in situ formed transition metal complexes exhibit a clear bleaching effect both with air and with H$_2$O$_2$ on a wide variety of stains.

What is claimed is:

1. A complex of the general formula (A1):

$$[M_aL_kX_n]Y_m \quad (A1)$$

in which:

M represents a metal selected from Mn(II)–(III)–(IV)–(V), Cu(I)–(II)–(III), Fe(II)–(III)–(IV)–(V), Co(I)–(II)–(III), Ti(II)–(III)–(IV), V(II)–(III)–(IV)–(V), Mo(II)–(III)–(IV)–(V)–(VI) and W(IV)–(V)–(VI);

X represents a coordinating species selected from any mono, bi or tri charged anions and any neutral molecules able to coordinate the metal in a mono, bi or tridentate manner;

Y represents any non-coordinated counter ion;

a represents an integer from 1 to 10;

k represents an integer from 1 to 10;

n represents an integer from 1 to 10;

m represents zero or an integer from 1 to 20; and

L represents a ligand of the general formula (I) or its protonated or deprotonated analogue:

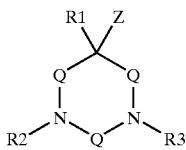

I wherein

Z represents a group selected from —$NH_2$, —$NHR^4$, —$N(R^4)_2$, —$N(R^4)_3^+$, —$NO_2$, —$NHC(O)R^4$, —$N(R^4)C(O)R^4$ wherein $R^4$ represents alkyl, cycloalkyl, aryl, arylalkyl or heteroarylalkyl, each optionally substituted by —F, —Cl, —Br, —I, —$NH_3^+$, —$SO_3H$, —$SO_3^-(Na^+, K^+)$, —COOH, —$COO^-(Na^+, K^+)$, —$P(O)(OH)_2$, or —$P(O)(O^-(Na^+, K^+))_2$; an optionally substituted heterocyclic ring or an optionally substituted heteroaromatic ring selected from pyridine, pyrimidine, pyrazine, pyrazole, imidazole, benzimidazole, quinoline, quinoxaline, triazole, isoquinoline, carbazole, indole, isoindole, oxazole and thiazole;

each Q independently represent a group of the formula:

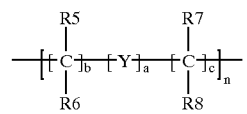

wherein $5 \geq a+b+c \geq 1$; a=0–5; b=–5; c=0–5; n=1 or 2;

Y independently represents a group selected from —O—, —S—, —SO—, —$SO_2$—, C(O)—, arylene, alkylene, heteroarylene, heterocycloalkylene, —(G)P—, —P(O)— and —(G)N—, wherein G is selected from hydrogen, alkyl, aryl, arylalkyl, cycloalkyl, each except hydrogen being optionally substituted by one or more functional groups E;

R1, R2, R3, R5, R6, R7, R8 independently represent a group selected from hydrogen, hydroxyl, halogen, —R and —OR, wherein R represents alkyl, alkenyl, cycloalkyl, heterocycloalkyl, aryl, heteroaryl or a carbonyl derivative group, R being optionally substituted by one or more functional groups E, or R5 together with R6, or R7 together with R8, or both, represent oxygen, or R5 together with R7 and/or independently R6 together with R8, or R5 together with R8 and/or Independently R6 together with R7, represent $C_{1-6}$-alkylene optionally substituted by $C_{1-4}$-alkyl, —F, —Cl, —Br or —I; and E independently represents a functional group selected from —F, —Cl, —Br, —I, —OH, —OR', —$NH_2$, —NHR', —$N(R')_2$, —$N(R')_3^+$, —C(O)R', —OC(O)R', —COOH, —$COO^-(Na^+, K^+)$, —COOR', —$C(O)NH_2$, —C(O)NHR', —$C(O)N(R')_2$, heteroaryl, —R', —SR', —SH, —$P(R')_2$, —$P(O)(R')_2$, —$P(O)(OH)_2$, —$P(O)(OR')_2$, —$NO_2$, —$SO_3H$, —$SO_3^-(Na^+, K^+)$, —$S(O)_2R'$, —NHC(O)R', and —N(R')C(O)R', wherein R' represents cycloalkyl, aryl, arylalkyl, or alkyl optionally substituted by —F, —Cl, —Br, —I, —$NH_3^+$, —$SO_3H$, —$SO_3^-(Na^+, K^+)$, —COOH, —$COO^-(Na^+, K^+)$, —$P(O)(OH)_2$, or —$P(O)(O^-(Na^+, K^+))_2$.

2. A complex according to claim 1, wherein in formula (A1):

X represents a coordinating species selected from $O^{2-}$, $RBO_2^{2-}$, $RCOO^-$, $RCONR^-$, $OH^-$, $NO_3^-$, NO, $S^{2-}$, $RS^-$, $PO_4^{3-}$, $PO_3OR^{3-}$, $H_2O$, $CO_3^{2-}$, $HCO_3^-$, ROH, NRR'R", $ROO^-$, $O_2^{2-}$, $O_2^-$, RCN, $Cl^-$, $Br^-$, $OCN^-$, $SCN^-$, $CN^-$, $N_3^-$, $F^-$, $I^-$, $RO^-$, $ClO_4^-$, and $CF_3SO_3^-$; and Y represents a counter ion selected from $ClO_4^-$, $BR_4^-$, $[MX_4]^-$, $[MX_4]^{2-}$, $PF_6^-$, $RCOO^-$, $NO_3^-$, $RO^-$, $N^+RR'R"R'''$, $ROO^-$, $O_2^{2-}$, $O_2^-$, $Cl^-$, $Br^-$, $F^-$, $I^-$, $CF_3SO_3^-$, $S_2O_6^{2-}$, $OCN^-$, $SCN^-$, $H_2O$, $RBO_2^{2-}$, $BF_4^-$ and $BPh_4^-$, wherein R, R', R", R''' independently represent a group selected 1from hydrogen, hydroxyl, —OR wherein R=alkyl, alkenyl, cycloalkyl, heterocycloalkyl, aryl, heteroaryl or carbonyl derivative group), alkyl, alkenyl, cycloalkyl, heterocycloalkyl, aryl, heteroaryl and carbonyl derivative groups, each of R, alkyl, alkenyl, cycloalkyl, heterocycloalkyl, aryl, heteroaryl and carbonyl derivative groups being optionally substituted by one or more functional groups E.

3. A complex according to claim 1, wherein in formula (A1):

M represents a metal selected from Mn(II)–(III)–(IV)–(V), Cu(I)–(II)–(III), Fe(II)–(III)–(IV) and Co(I)–(II)–(III);

X represents a coordinating species selected from $O^{2-}$, $RBO_2^{2-}$, $RCOO^-$, $OH^-$, $NO_3^-$, $S^{2-}$, $RS^-$, $PO_3^{4-}$, $H_2O$, $Co_3^{2-}$, $HCO_3^-$, ROH, NRR'R", $Cl^-$, $Br^-$, $OCN^-$, $SCN^-$, RCN, $N_3^-$, $F^-$, $I^-$, $RO^-$, $ClO_4^-$, and $CF_3SO_3^-$;

Y represents a counter ion selected from $ClO_4^-$, $BR_4^-$, $[FeCl_4]^-$, $PF_6^-$, $RCOO^-$, $NO_3^-$, $RO^-$, $N^+RR'R"R'''$, $Cl^-$, $Br^-$, $F^-$, $I^-$, $CF_3SO_3^-$, $S_2O_6^{2-}$, $OCN^-$, $SCN^-$, $H_2O$ and $BF_4^-$, wherein R, R', R", R''' represent represent hydrogen, optionally substituted alkyl or optionally substituted aryl;

a represents an integer from 1 to 4;

k represents an integer from 1 to 10;

n represents an integer from 1 to 4; and m represents zero or an integer from 1 to 8.

4. A bleaching composition comprising, in an aqueous medium, atmospheric oxygen and a ligand which forms a complex with a transition metal, the complex catalysing bleaching of a substrate by the atmospheric oxygen, wherein the ligand is a compound as defined by general formula (I) and the aqueous medium is substantially devoid of peroxygen bleach or a peroxy-based or -generating system, the general formula being:

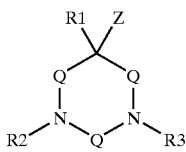

wherein

Z represents a group selected from —NH$_2$, —NHR$^4$, —N(R$^4$)$_2$, —N(R$^4$)$_3^+$, —NO$_2$, —NHC(O)R$^4$, —N(R$^4$)C(O)R$^4$ (wherein R$^4$ represents alkyl, cycloalkyl, aryl, arylalkyl or heteroarylalkyl, each optionally substituted by —F, —Cl, —Br, —I, —NH$_3^+$, —SO$_3$H, —SO$_3^-$ (Na$^+$, K$^+$), —COOH, —COO$^-$(Na$^+$, K$^+$), —P(O)(OH)$_2$, or —P(O)(O$^-$(Na$^+$, K$^+$))$_2$), an optionally substituted heterocyclic ring or an optionally substituted heteroaromatic ring selected from pyridine, pyrimidine, pyrazine, pyrazole, imidazole, benzimidazole, quinoline, quinoxaline, triazole, isoquinoline, carbazole, indole, isoindole, oxazole and thiazole;

each Q independently represent a group of the formula:

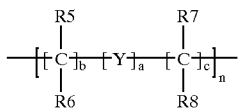

wherein $5 \geq a+b+c \geq 1$; $a=0-5$; $b=0-5$; $c=0-5$; $n=1$ or 2;

Y independently represents a group selected from —O—, —S—, —SO—, —SO$_2$—, —C(O)—, arylene, alkylene, heteroarylene, heterocycloalkylene, —(G)P—, —P(O)— and —(G)N—, wherein G is selected from hydrogen, alkyl, aryl, arylalkyl, cycloalkyl, each except hydrogen being optionally substituted by one or more functional groups E;

R1, R2, R3, R5, R6, R7, R8 independently represent a group selected from hydrogen, hydroxyl, halogen, —R and —OR, wherein R represents alkyl, alkenyl, cycloalkyl, heterocycloalkyl, aryl, heteroaryl or a carbonyl derivative group, R being optionally substituted by one or more functional groups E, or R5 together with R6, or R7 together with R8, or both, represent oxygen, or R5 together with R7 and/or independently R6 together with R8, or R5 together with R8 and/or independently R6 together with R7, represent C$_{1-6}$-alkylene optionally substituted by C$_{1-4}$-alkyl, —F, —Cl, —Br or —I; and E independently represents a functional group selected from —F, —Cl, —Br, —I, —OH, —OR', —NH$_2$, —NHR', —N(R')$_2$, —N(R')$_3^+$, —C(O)R', —OC(O)R', —COOH, —COO$^-$(Na$^+$, K$^+$), —COOR', —C(O)NH$_2$, —C(O)NHR', —C(O)N(R')$_2$, heteroaryl, —R', —SR', —SH, —P(R')$_2$, —P(O)(R')$_2$, —P(O)(OH)$_2$, —P(O)(OR')$_2$, —NO$_2$, —SO$_3$H, —SO$_3^-$(Na$^+$, K$^+$), —S(O)$_2$R', —NHC(O)R', and —N(R')C(O)R', wherein R' represents cycloalkyl, aryl, arylalkyl, or alkyl optionally substituted by —F, —Cl, —Br, —I, —NH$_3^+$, —SO$_3$H, —SO$_3^-$(Na$^+$, K$^+$), —COOH, —COO$^-$(Na$^+$, K$^+$), —P(O)(OH)$_2$, or —P(O)(O$^-$(Na$^+$, K$^+$))$_2$.

5. A bleaching composition according to claim 4, wherein the medium is substantially devoid of a transition metal sequestrant.

6. A bleaching composition comprising, in an aqueous medium, a ligand which forms a complex with a transition metal, the complex catalysing bleaching of a substrate, and a peroxygen bleach or a peroxy-based or -generating system, wherein the ligand is a compound as defined by the general formula (I):

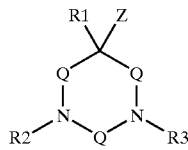

wherein

Z represents a group selected from —NH$_2$, —NHR$^4$, —N(R$^4$)$_2$, —N(R$^4$)$_3^+$, —NO$_2$, —NHC(O)R$^4$, —N(R$^4$)C(O)R$^4$ (wherein R$^4$ represents alkyl, cycloalkyl, aryl, arylalkyl or heteroarylalkyl, each optionally substituted by —F, —Cl, —Br, —I, —NH$_3^+$, —SO$_3$H, —SO$_3^-$ (Na$^+$, K$^+$), —COOH, —COO$^-$(Na$^+$, K$^+$), —P(O)(OH)$_2$, or —P(O)(O$^-$(Na$^+$, K$^+$))$_2$), an optionally substituted heterocyclic ring or an optionally substituted heteroaromatic ring selected from pyridine, pyrimidine, pyrazine, pyrazole, imidazole, benzimidazole, quinoline, quinoxaline, trazole, isoquinoline, carbazole, indole, isoindole, oxazole and thiazole;

each Q independently represent a group of the formula:

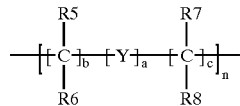

wherein $5 \geq a+b+c \geq 1$; $a=0-5$; $b=0-5$; $c=0-5$; $n=1$ or 2;

Y Independently represents a group selected from —O—, —S—, —SO—, —SO$_2$—, —C(O)—, arylene, alkylene, heteroarylene, heterocycloalkylene, —(G)P—, —P(O)— and —(G)N—, wherein G is selected from hydrogen, alkyl, aryl, arylalkyl, cycloalkyl, each except hydrogen being optionally substituted by one or more functional groups E;

R1, R2, R3, R5, R6, R7, R8 independently represent a group selected from hydrogen, hydroxyl, halogen, —R and —OR, wherein R represents alkyl, alkenyl, cycloalkyl, heterocycloalkyl, aryl, heteroaryl or a carbonyl derivative group, R being optionally substituted by one or more functional groups E, or R5 together with R6, or R7 together with R8, or both, represent oxygen, or R5 together with R7 and/or independently R6 together with R8, or R5 together with R8 and/or Independently R6 together with R7, represent C$_{1-6}$-alkylene optionally substituted by C$_{1-4}$-alkyl, —F, —Cl, —Br or —I; and E independently represents a functional group selected from , —Cl, —Br, —I, —OH, —OR', —NH$_2$, —NHR', —N(R')$_2$; —N(R')$_3^+$, —C(O)R', —OC(O)R', —COOH, —COO$^-$(Na$^+$, K$^+$), —COOR', —C(O)NH$_2$, —C(O)NHR', —C(O)N(R')$_2$, heteroaryl, —R', —SR', —SH, —P(R')$_2$, —P(O)(R')$_2$, —P(O)(OH)$_2$, —P(O)(OR')$_2$, —NO$_2$, —SO$_3$H, —SO$_3^-$(Na$^+$, K$^+$), —S(O)2R', —NHC(O)R', and —N(R')C(O)R', wherein R' represents cycloalkyl, aryl, arylalkyl, or alkyl optionally substituted by —F, —Cl, —Br, —I, —NH$_3^+$, —SO$_3$H, —SO$_3^-$(Na$^+$, K$^+$), —COOH, —COO$^-$(Na$^+$, K$^+$), —P(O)(OH)$_2$, or —P(O)(O$^-$(Na$^+$, K$^+$))$_2$.

7. A bleaching composition according to claim 6, wherein the medium has a pH value in the range from pH 6 to 11, preferably in the range from pH 8 to 10.

8. A bleaching composition according to claim 7, wherein the medium further comprises a surfactant.

9. A bleaching composition according to claim 8, wherein the medium further comprises a builder.

10. A bleaching composition according to claim 9, wherein the composition comprises a preformed complex of the ligand and a transition metal.

11. A bleaching composition according to claim 4, wherein the ligand is present as a free ligand that complexes with a transition metal present in the water.

12. A bleaching composition according to claim 4, wherein the ligand is present as a free ligand that complexes with a transition metal present in the substrate.

13. A bleaching composition according to claim 4, wherein the composition comprises the ligand present as a free ligand or a transition metal-substitutable metal-ligand complex, and a source of transitional metal.

14. A method of bleaching a substrate comprising applying to the substrate, in an aqueous medium, a ligand which forms a complex with a transition metal, the complex catalysing bleaching of the substrate by atmospheric oxygen, wherein the ligand is a compound as defined by the general formula (I) and the medium is substantially devoid of peroxygen bleach or a peroxy-based or -generating bleach system, the general formula being:

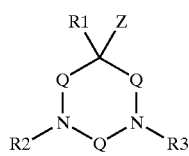

I wherein

Z represents a group selected from —NH$_2$, —NHR$^4$, —N(R$^4$)$_2$, —N(R$^4$)$_3^+$, —NO$_2$, —NHC(O)R$^4$, —N(R$^4$)C(O)R$^4$ (wherein R$^4$ represents alkyl, cycloalkyl, aryl, arylalkyl or heteroarylalkyl, each optionally substituted by —F, —Cl, —Br, —I, —NH$_3^+$, —SO$_3$H, —SO$_3^-$(Na$^+$, K$^+$), —COOH, —COO$^-$(Na$^+$, K$^+$), —P(O)(OH)$_2$, or —P(O)(O$^-$(Na$^+$, K$^+$))$_2$, an optionally substituted heterocyclic ring or an optionally substituted heteroaromatic ring selected from pyridine, pyrimidine, pyrazine, pyrazole, imidazole, benzimidazole, quinoline, quinoxaline, triazole, isoquinoline, carbazole, indole, isoindole, oxazole and thiazole;

each Q independently represent a group of the formula:

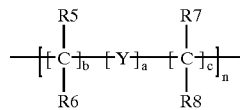

wherein $5 \geq a+b+c \geq 1$; a=0–5; b=0–5; c=0–5; n=1 or 2;

Y independently represents a group selected from —O—, —S—, —SO—, —SO$_2$—, —C(O)—, arylene, alkylene, heteroarylene, heterocycloalkylene, —(G)P—, —P(O)— and —(G)N—, wherein G is selected from hydrogen, alkyl, aryl, arylalkyl, cycloalkyl, each except hydrogen being optionally substituted by one or more functional groups E;

R1, R2, R3, R5, R6, R7, R8 independently represent a group selected from hydrogen, hydroxyl, halogen, —R and —OR, wherein R represents alkyl, alkenyl, cycloalkyl, heterocycloalkyl, aryl, heteroaryl or a carbonyl derivative group, R being optionally substituted by one or more functional groups E, or R5 together with R6, or R7 together with R8, or both, represent oxygen, or R5 together with R7 and/or independently R6 together with R8, or R5 together with R8 and/or independently R6 together with R7, represent C$_{1-6}$-alkylene optionally substituted by C$_{1-4}$-alkyl, —F, —Cl, —Br or —I; and E independently represents a functional group selected from —F, —Cl, —Br, —I, —OH, —OR', —NH$_2$, —NHR', —N(R')$_2$, —N(R')$_3^+$, —C(O)R', —OC(O)R', —COOH, —COO$^-$(Na$^+$, K$^+$), —COOR', —C(O)NH$_2$, —C(O)NHR', —C(O)N(R')$_2$, heteroaryl, —R', —SR', —SH, —P(R')$_2$, —P(O)(R')$_2$, —P(O)(OH)$_2$, —P(O)(OR')$_2$, —NO$_2$, —SO$_3$H, —SO$_3^-$(Na$^+$, K$^+$), —S(O)$_2$R', —NHC(O)R', and —N(R')C(O)R', wherein R' represents cycloalkyl, aryl, arylalkyl, or alkyl optionally substituted by —F, —Cl, —Br, —I, —NH$_3^+$, —SO$_3$H, —SO$_3^-$(Na$^+$, K$^+$), —COOH, —COO$^-$(Na$^+$, K$^+$), —P(O)(OH)$_2$, or —P(O)(O$^-$(Na$^+$, K$^+$))$_2$.

15. A method according to claim 14, wherein the majority of the bleaching species in the medium (on an equivalent weight basis) is derived from the atmospheric oxygen.

16. A method of bleaching a substrate comprising applying to the substrate, in an aqueous medium, a ligand which forms a complex with a transition metal, wherein the ligand is a compound as defined by general formula (I) and the medium comprises a peroxygen bleach or a peroxy-based or -generating system, the general formula being:

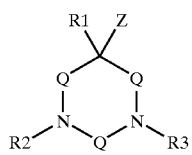

I wherein

Z represents a group selected from —NH$_2$, —NHR$^4$, —N(R$^4$)$_2$, —N(R$^4$)$_3^+$, —NO$_2$, —NHC(O)R$^4$, —N(R$^4$)C(O)R$^4$ (wherein R$^4$ represents alkyl, cycloalkyl, aryl, arylalkyl or heteroarylalkyl, each optionally substituted by —F, —Cl, —Br, —I, —NH$_3^+$, —S$_3$H, —SO$_3^-$(Na$^+$, K$^+$), —COOH, —COO$^-$(Na$^+$, K$^+$), —P(O)(OH)$_2$, or —P(O)(O$^-$(Na$^+$, K$^+$))$_2$, an optionally substituted heterocyclic ring or an optionally substituted heteroaromatic ring selected from pyridine, pyrimidine, pyrazine, pyrazole, imidazole, benzimidazole, quinoline, quinoxaline, triazole, isoquinoline, carbazole, indole, isoindole, oxazole and thiazole;

each Q independently represent a group of the formula:

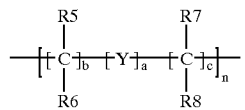

wherein $5 \geq a+b+c \geq 1$; $a=0-5$; $b=0-5$; $c=0-5$; $n=1$ or $2$;

Y independently represents a group selected from —O—, —S—, —SO—, —SO$_2$—, —C(O)—, arylene, alkylene, heteroarylene, heterocycloalkylene, —(G)P—, —P(O)— and —(G)N—, wherein G is selected from hydrogen, alkyl, aryl, arylalkyl, cycloalkyl, each except hydrogen being optionally substituted by one or more functional groups E;

R1, R2, R3, R5, R6, R7, R8 independently represent a group selected from hydrogen, hydroxyl, halogen, —R and —OR, wherein R represents alkyl, alkenyl, cycloalkyl, heterocycloalkyl, aryl, heteroaryl or a carbonyl derivative group, R being optionally substituted by one or more functional groups E, or R5 together with R6, or R7 together with R8, or both, represent oxygen, or R5 together with R7 and/or independently R6 together with R8, or R5 together with R8 and/or independently R6 together with R7, represent C$_{1-6}$-alkylene optionally substituted by C$_{1-4}$-alkyl, —F, —Cl, —Br or —I; and E independently represents a functional group selected from —F, —Cl, —Br, —I, —OH, —OR', —NH$_2$, —NHR', —N(R')$_2$, —N(R')$_3^-$, —C(O)R', —OC(O)R', —COOH, —COO$^-$(Na$^+$, K$^+$), —COOR', —C(O)NH$_2$, —C(O)NHR', —C(O)N(R')$_2$, heteroaryl, —R', —SR', —SH, —P(R')$_2$, —P(O)(R')$_2$, —P(O)(OH)$_2$, —P(O)(OR')$_2$, —NO$_2$, —SO$_3$H, —SO$_3^-$(Na$^+$, K$^+$), —S(O)$_2$R', —NHC(O)R', and —N(R')C(O)R', wherein R' represents cycloalkyl, aryl, arylalkyl, or alkyl optionally substituted by —F, —Cl, —Br, —I, —SO$_3$H, —SO$_3^-$((Na$^+$, K$^+$), —COOH, —COO$^-$(Na$^+$, K$^+$), —P(O)(OH)$_2$, or —P(O)(O$^-$(Na$^+$, K$^+$))$_2$.

* * * * *

UNITED STATES PATENT AND TRADEMARK OFFICE
CERTIFICATE OF CORRECTION

PATENT NO. : 6,537,959 B2
DATED : March 25, 2003
INVENTOR(S) : Appel et al.

It is certified that error appears in the above-identified patent and that said Letters Patent is hereby corrected as shown below:

<u>Title page,</u>
Item [56], FOREIGN PATENT DOCUMENTS, includes the following:
-- EP   0 331 229      2/89
   EP   0 384 070      11/89
   EP   0 458 396      11/91
   EP   0 464 880      5/91
   WO   95/07972       3/95
   WO   95/34628       12/95
   WO   97/38074       10/97
   WO   97/48787       10/97
   WO   98/39406       9/98 --

Signed and Sealed this

Nineteenth Day of August, 2003

JAMES E. ROGAN
*Director of the United States Patent and Trademark Office*